United States Patent
Giglia et al.

(10) Patent No.: US 8,733,556 B2
(45) Date of Patent: May 27, 2014

(54) METHOD FOR REDUCING PERFORMANCE VARIABILITY OF MULTI-LAYER FILTERS

(75) Inventors: Sal Giglia, Billerica, MA (US); Mani Krishnan, Billerica, MA (US); Nitin Satav, Billerica, MA (US)

(73) Assignee: EMD Millipore Corporation, Billerica, MA (US)

( * ) Notice: Subject to any disclaimer, the term of this patent is extended or adjusted under 35 U.S.C. 154(b) by 505 days.

(21) Appl. No.: 12/387,576

(22) Filed: May 5, 2009

(65) Prior Publication Data

US 2009/0277835 A1 Nov. 12, 2009

Related U.S. Application Data

(60) Provisional application No. 61/127,156, filed on May 9, 2008.

(51) Int. Cl.
| | |
|---|---|
| *B01D 71/68* | (2006.01) |
| *B01D 69/06* | (2006.01) |
| *B01D 29/56* | (2006.01) |
| *B01D 61/00* | (2006.01) |
| *B01D 69/02* | (2006.01) |
| *B01D 61/14* | (2006.01) |

(52) U.S. Cl.
CPC ............... *B01D 69/02* (2013.01); *B01D 71/68* (2013.01); *B01D 29/56* (2013.01); *B01D 61/14* (2013.01); *B01D 2325/02* (2013.01); *B01D 2239/069* (2013.01)
USPC .............. 210/500.22; 210/500.21; 210/490; 210/650

(58) Field of Classification Search
None
See application file for complete search history.

(56) References Cited

U.S. PATENT DOCUMENTS

| | | | |
|---|---|---|---|
| 5,017,292 A | 5/1991 | DiLeo et al. | 210/645 |
| 5,457,986 A | 10/1995 | DiLeo et al. | 73/38 |
| 5,490,937 A | 2/1996 | Van Reis | 210/637 |
| 5,968,373 A | 10/1999 | Choi | 210/806 |
| 6,019,809 A | 2/2000 | Kahlbaugh et al. | 55/486 |
| 6,669,905 B1 | 12/2003 | Mathias et al. | 422/44 |
| 6,872,431 B2 | 3/2005 | Kahlbaugh et al. | 428/36.1 |
| 7,108,791 B2 | 9/2006 | Tkacik et al. | 210/651 |

(Continued)

FOREIGN PATENT DOCUMENTS

| | | | |
|---|---|---|---|
| JP | 10-024224 A | 6/1990 | |
| JP | 7-124450 A | 5/1995 | |

(Continued)

OTHER PUBLICATIONS

JTATM (Journal of Textile and Apparel, Technology and Management) vol. 5, Issue 3, Fall 2006; Hongqing Shen; "Study of Layering Order on Filtration Ability of Surgical Face Masks".
Adv. Mater. 2006, 18, 709-712; Seung Y. Yang et al.; "Nanoporous Membranes With Ultrahigh Selectivity and Flux for the Filtration of Virsuses".

(Continued)

*Primary Examiner* — Krishnan S Menon
(74) *Attorney, Agent, or Firm* — Nields, Lemack & Frame, LLC

(57) ABSTRACT

Multi-layer membrane devices with reduced performance variability, and method of reducing performance variability of such devices. The variability is reduced by combining two or more membranes with similar pore sizes, and carefully selecting the upstream membrane based upon its performance rating, in order to control the performance of the overall device. Selective layering reduces the capacity range of the device when compared to random layering, with the mean capacity greater than overall population mean. The flux range also can be reduced, with the mean near the overall population mean. The LRV range also can be reduced, with the mean LRV near or higher than the overall population mean.

12 Claims, 4 Drawing Sheets

(56) References Cited

U.S. PATENT DOCUMENTS

| 2002/0175124 A1 | 11/2002 | Tkacik et al. ............... 210/651 |
| 2003/0209485 A1 | 11/2003 | Kools ........................... 210/490 |
| 2007/0187319 A1 | 8/2007 | Kools et al. ............ 210/500.27 |
| 2008/0028834 A1 | 2/2008 | Gevers et al. ..................... 73/38 |
| 2009/0277824 A1 | 11/2009 | Giglia et al. |

FOREIGN PATENT DOCUMENTS

| JP | 7-167852 A | 7/1995 |
| JP | 2-167232 A | 1/1998 |
| JP | 2003-509189 A | 3/2003 |
| JP | 2003-144128 | 5/2003 |
| WO | 01/19506 A1 | 3/2001 |
| WO | 02/05934 | 1/2002 |

OTHER PUBLICATIONS

Journal of Membrane Science 169 (2000) 255-268; Chung-Yi Tsai et al.; "Dual-Layer Asymmetric Microporous Silica Membranes".

Japanese Communication, with English translation, dated Jan. 25, 2011 in corresponding foreign application JP 2009-113594.

Office Action dated Feb. 4, 2011 in corresponding U.S. Appl. No. 12/387,636.

Japanese Communication, with English translation, mailed Feb. 28, 2012 in corresponding Japanese Patent Application No. 2009-113594.

Final Rejection dated Aug. 26, 2011 in corresponding U.S. Appl. No. 12/387,636.

Millipore Data Sheet, 2002, Lit. No. DS1180EN00, "Viresolve 70 and 180 Modules with CorrTest Integrity Test Kits", 8 pages.

Millipore Application Note article, 2003, Lit No. PF2001EN00, "Using a New, Fast Flow, Low Protein Binding Membrane for Sterile Filtration", 4 pages, Gabriels.

Final Rejection mailed Jan. 8, 2014 in corresponding U.S. Appl. No. 12/387,636.

METHOD FOR REDUCING PERFORMANCE VARIABILITY OF MULTI-LAYER FILTERS

This application claims priority of U.S. Provisional application Ser. No. 61/127,156 filed May 9, 2008, the disclosure of which is incorporated herein by reference.

BACKGROUND OF THE INVENTION

Virus contamination poses a threat to the safety of biopharmaceuticals derived from recombinant or human plasma sources. Manufacturing processes must provide clearance of endogenous and adventitious viruses to ensure product safety. To that end, filters have been developed that provide virus removal. To be commercially effective and cost-efficient, such filters must provide effective virus removal while maximizing product recovery, and must be reliable, consistent and capable of validation.

Virus removal from liquid streams, particularly process streams in the biotech and pharmaceutical industry, has been practiced for some time. High viral clearance, high product flux, very high protein passage and simplicity of operation are the goals of the end-user, yet the prior art does not provide a solution that satisfies all of these goals. Since high viral clearance is always needed, it is the other process goals that have suffered. Meeting these other goals would substantially increase production efficiency and thus lower processing cost.

The prior art provides several membrane types and filtration modes for viral clearance. One such product is the Viresolve NFR filters with Retropore® membrane that is used to remove retroviruses from recombinant protein solutions or human plasma sources. U.S. Pat. No. 7,108,791 B2 discloses a virus removal methodology using Viresolve NFR filters, suitable for conducting a high-flux fluid separation of virus from a protein in the course of biopharmaceutical manufacture, the methodology comprising the steps of: (a) providing a filtration device comprising a housing having a fluid inlet and a filtrate outlet, and containing at least two interfacially contiguous asymmetric membranes, wherein: (i) the asymmetric membranes are each substantially hydrophilic, (ii) at least two of the hydrophilic membranes are each capable of substantially selectively preventing the passage therethrough of said virus and substantially permitting the passage therethrough of said protein, (iii) at least two of the asymmetric membranes have each a tight-side and open-side, (iv) the foremost asymmetric membrane is oriented such that fluid introduced in said housing through the fluid inlet commences passage through said foremost asymmetric membrane through its open side. It also claims that each of said asymmetric membranes are substantially identical in their composition and porosity, and wherein the porosity of each said asymmetric membranes is defined to enable performance of the virus removal methodology, yielding a log reduction value (LRV) greater than 6 and a protein passage greater than 98%.

Consistency in device-to-device performance is critically important for users of membrane filtration devices in order to predict filtration performance from run to run, and to scale-up or otherwise engineer and design processes. Users often cite performance consistency as one of the most important factors in filter selection. In the case of bacterial or virus filtration, the performance criteria important to users include throughput capacity, flux (or permeability), and retention of bacteria or viruses.

Capacity is important in high value filtration processes such as virus removal in biopharmaceutical manufacturing. Capacity relates to the length of time, or volume of fluid that can be filtered before the filtration rate is reduced through plugging by retained species or fouling, etc., to an uneconomic level. High capacity filtration improves process economics by reducing processing time and the amount of filter area required. High flux becomes critical in medium- and large-scale manufacturing operations where process equipment is required to be turned around rapidly to process the next batch of product. In all these operations, repeatability of filter performance from batch to batch is very important.

Performance variability may depend on a number of factors such as membrane variability, lot-to-lot protein variability, variability in operating parameters, etc. Manufacturers of the therapeutic proteins take measures to minimize lot-to-lot protein variability. Membrane variability can be defined by the difference of properties from manufacturing lot to lot. A manufacturing lot, or batch, the terms are interchangeable, is defined by the manufacturer. A lot can be the production output from a single polymer solution volume in immersion casting, or the output from an operating shift. It is common in flat sheet membrane to label each manufactured roll as a lot or sub-lot. A single roll or lot may also be subdivided based on the variability within that roll. There are many factors that influence membrane performance, including the pore size distribution, the membrane chemistry, membrane thickness, membrane porosity, and others. While membrane manufacturing processes are designed to control all of these factors to maximize uniformity and consistency, there will inevitably be some distribution within normal manufacturing conditions for all of these variables. This membrane variability contributes to device-to-device performance consistency. Methods used to reduce variability in a device through selective layering is described herein.

In addition to reducing device variability, membrane device manufacturers desire to optimize and/or maximize device properties of a population of devices. As will be described, embodiments herein provide for methods to increase the average capacity (defined below) of a population of manufactured devices through selective layering as compared to a population manufactured by standard non-selective layering.

The ability to control device consistency is particularly important for multilayered filtration devices. For these devices, not only is the variability of the membrane important, but membrane variability can affect the interaction between the layers, as will be shown below.

It therefore would be desirable to provide a multi-layer membrane device with reduced performance variability, as well as a method of reducing the performance variability of such devices, notwithstanding the inherent variability of the membrane manufacturing process.

SUMMARY OF THE INVENTION

Aspects of the discoveries of the inventors provide multi-layer membrane filtration devices with reduced performance variability. The variability is reduced by combining two or more membranes with similar pore sizes, and carefully selecting the upstream membrane based upon its performance rating, in order to control the performance of the overall device.

The upstream or top membrane layer is the membrane layer that the feed stream fluid initially contacts and passes through. Conversely, the bottom layer is the last layer the fluid contacts and passes through.

The membranes do not necessarily need to be stacked. They can be separated within the device, or even contained within separate devices. The membrane/device format is not limited to flat sheets, but can be in any format including pleated, spiral, or hollow fiber and can be applied to devices that are operated either in normal (or dead-ended) flow or tangential flow methods.

In an embodiment, selective layering in accordance with the invention reduces the capacity range of the devices when compared to random or non-selective layering. Range is defined as the difference between the high and low value of a property of a population of devices.

In an embodiment, the mean capacity of a population of devices is greater than overall population mean of the individual membrane lots used to manufacture the population.

In an embodiment, the capacity of a multilayered device produced from layers of different capacity is higher that the arithmetic average of the individual layers.

In an embodiment, the flux (or permeability) range is reduced, with the mean near the overall population mean.

In an embodiment, the LRV range is reduced, with the mean LRV near or higher than the overall population mean.

In an embodiment, the filtration capacity of a population of multilayered filter devices manufactured from membrane lots or a single lot having capacity property variability is maximized.

DETAILED DESCRIPTION OF THE INVENTION

Figure 1:
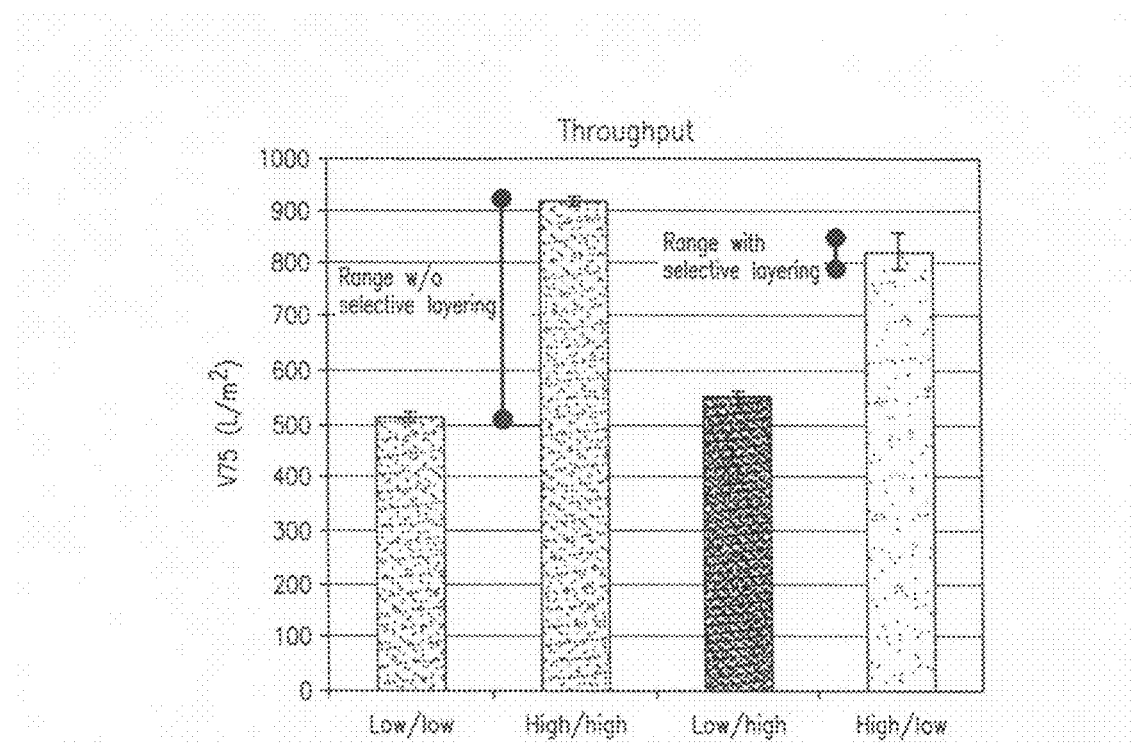
FIG. 1 is a bar graph showing throughput of 2-layer membrane devices containing high and low capacity membranes combined in different positions with respect to top (upstream) and bottom (downstream) position.

Membrane manufacturing processes inherently result in some variability in membrane properties even though materials and process conditions are kept as constant as possible. Manufacturers typically carry out a battery of tests on membrane lots to ensure that the manufacturing process has produced membrane within established limits. Additionally, procedures can also be instituted to classify or "rate" each batch. or roll of membranes after manufacture, based on performance. Membrane manufacturers use a variety of methods to rate membranes. For example, for microporous membranes, versions of the well known bubble point test may be used to give a pore size rating. ASTM F-838-05 describes a method of LRV rating using b. diminuta. Ultrafiltration membranes are rated by testing with water soluble polysaccharides as described, for example, in G. Tkacik and S. Michaels, "A rejection profile test for ultrafiltration membranes and devices", Bio/Technology 9, 941 (1991).

Membrane lots to be incorporated into multilayered devices for virus removal in biotherapeutics manufacturing may be tested by normal flow log reduction value (LRV)/ capacity tests which challenge the membrane with the bacteriophage, such as $\phi$x-174, in a protein solution, such as bovine serum albumin (BSA), or human IgG. Virus retention (LRV) and capacity (volume filtered) at a predetermined end-point, such as 70-75% flow reduction, are measured, and relative performance values are obtained. Typically, water or another appropriate fluid, is used to measure permeability of the membrane.

The membranes from the given batch are then performance rated based upon the results obtained. All the membranes are qualified under a single standard of permeability, retention and capacity. That is, all qualified membrane is considered as a single product meeting all specifications with regard to form, function and performance (including pore size rating). As with any product, there are tolerances in the specifications. Regardless of the tightness of the tolerances, there will inevitably be some finite performance variability within the specification tolerance range.

It is known that for stacked filters, the resistance to flow is additive, so that the flux of the stack will be approximately the average of the filters used to make the stack. Also, retention, as measured by LRV, is approximately additive, so that the LRV of a stack will be approximately the sum of the LRV's of the individual layers. However, the present inventors have surprisingly found that for multi-layer devices containing similarly rated membranes in each of the layers, the contribution of each layer to performance of the device does not necessarily follow such a predictable response, particularly where performance is defined in terms of capacity.

The present inventors have found that by providing multi-layer devices containing similarly rated membranes in each of the layers, each layer within the device contributes to performance. However, the contribution of each layer to performance of the device generally is not equal, particularly where performance is defined in terms of capacity. As used herein, the term "capacity" is the volume of fluid that can be processed by the membrane before reaching a practical endpoint. In the case of constant pressure filtration, for example, that endpoint is defined as the condition at which the flux has decayed due to membrane fouling to a predetermined minimum.

The present inventors have found that in a multi-layer device containing similarly rated membranes, the upstream layer controls throughput capacity. Moreover, the inventors were surprised to discover that when selective layering was employed, the average capacity of a device, or of a population of devices, was higher that the average of the individual layers. Accordingly, once the capacity of each membrane of the lots to be used to make a population of devices is known, the upstream membrane of a multi-layer membrane device can be selected according to the methods herein to obtain the highest capacity for a single device, or the highest average for the population manufactured. As well, the range of capacity values for the device population will be smaller than that of the population of membranes from whence the devices were made. Additional performance criteria, such as retention and/ or permeability, also can be used to measure performance, and to base membrane selection on.

Added benefits are that the while the resultant flux of the selectively layered device is approximately the average of the layers, the range of values is smaller that that of the membranes used. The resulting LRV of selectively layered devices is similar to the average of the membranes used, with a smaller range.

Figure 2:
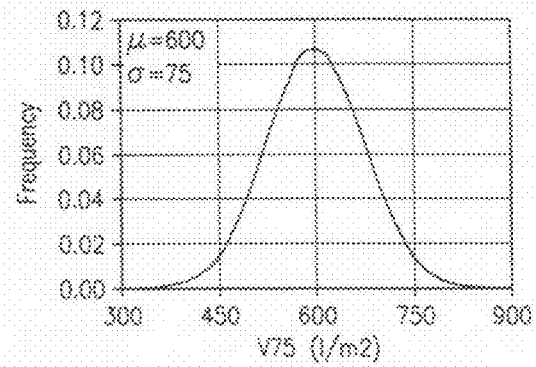
FIG. 2 is a graph of a hypothetical distribution of membrane capacities.

By way of example, the effect of layer ordering on capacity can be demonstrated on normal flow virus filtration membranes, although the present invention is not so limited. FIG. 1 shows that a double layer membrane capacity (defined as 75% flow decay from the initial non-fouled value) of an asymmetric polyethersulfone membrane commercially available from Millipore Corporation under the name VIRESOLVE PRO™, is controlled primarily by the capacity of the upstream layer membrane, regardless of the capacity of the bottom layer membrane. Thus, for the membrane roll designated as "low" capacity, two layers of this membrane had a throughput of about 500 L m². For the membrane roll designated as "high" capacity, two layers of this membrane had a throughput of about 900 L/m². Throughput and capacity are equivalent terms. When "high" membranes were positioned upstream over "low" membranes that were placed in the downstream position, the capacity of these devices were nearly equivalent to that of devices that contained two layers of "high" membrane. A similar result is apparent for membranes where the "low" capacity membranes were positioned upstream over "high" capacity membranes that were placed in the downstream position. The capacity of the multi-layer device was not negatively impacted by the relatively low throughput of the bottom layer membrane. The "low/high" combination shows that despite the relatively high capacity of the downstream layer, again the overall capacity of the multi-layer device is a function primarily of the upstream layer. Accordingly, if two or more membranes of known differing capacities are available for assembly into a multi-layer membrane device, the membrane available with the highest capacity can be selected as the upstream layer. To explain the selective layering approach, the capacity properties of membrane lots available to be made into devices is approximately formulated into a distribution as illustrated in FIG. 2. A portion of the membrane capacity distribution is then selected as top layer membrane in order to reduce the range of device capacities compared to layering the membranes randomly, and to maximize capacity and/or minimize device-to-device capacity variability.

This phenomenon has also been demonstrated on three-layer Optiscale-25 devices with Viresolve NFP membrane (Millipore Corporation, Billerica, Mass.). Viresolve NFP (Normal Flow Parvovirus) membranes clear parvovirus from recombinant or human plasma sources. U.S. Pat. No. 5,017,292 discloses technology used to produce the Viresolve membrane. It provides a composite PVDF membrane comprising a porous membrane substrate and a tight side (the surface having smaller diameter pores) having ultrafiltration separation properties.

To demonstrate the effect on capacity, NFP membrane rolls with a range of average capacities were selected and labeled as high (H), mid (M) and low (L) capacity rolls.

Devices were built with various combinations, for example: HHH, HLL, MHH, MLL, LHH, LLL, etc. The first, second and third letter indicate upstream, middle and downstream layers, respectively, as shown below

|   | H | M | L |
|---|---|---|---|
|   | H | H | H |
|   | H | H | H |

Figure 1A:
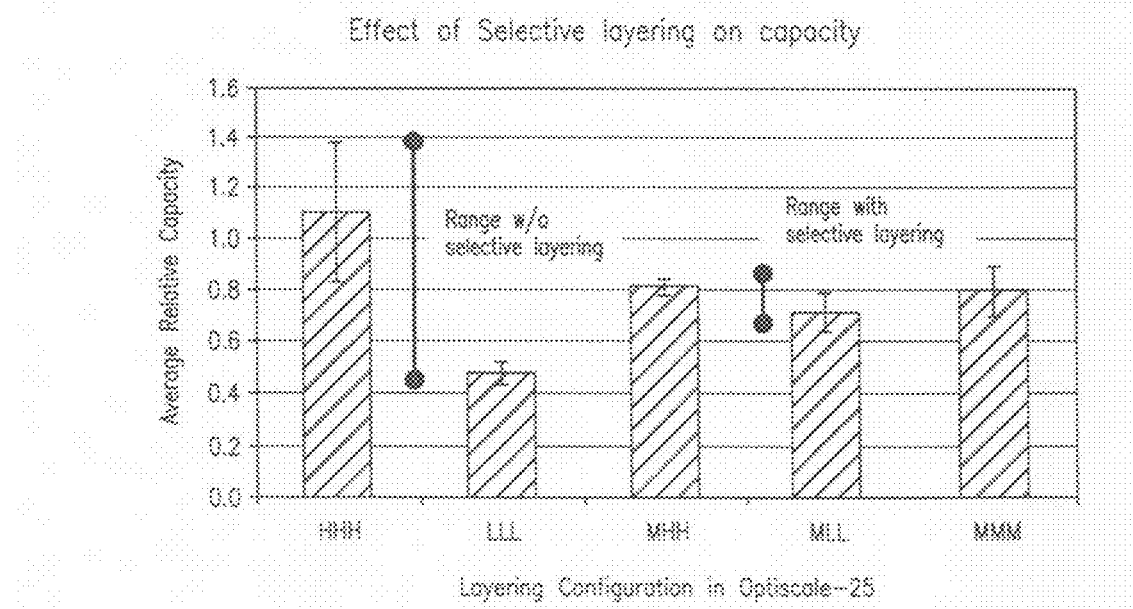
FIG. 1a is a graph showing throughput of 3-layer devices containing high, medium, and low capacity membranes combined in different positions with respect to top (upstream), middle and bottom (downstream) position.

These optiscales were tested for capacity using a BSA stream spiked with φx-174. FIG. 1A shows relative capacity values for different layering combinations.

These results showed that when "Mid" capacity membrane (MMM) was used as a top layer over "High" capacity (HHH) or "Low" capacity (LLL) membranes, then devices with layered combination (MHH or MLL) showed capacity close to Mid capacity membrane. In other words, variability in relative capacity was reduced as a result of selectively placing "mid" capacity membrane as top layer. In this particular example, the range in relative capacity was reduced from about −1.0 to about 0.2.

Accordingly, if two or more membranes of known differing capacities are available for assembly into a multi-layer membrane device, the membrane with the capacity closest to the target capacity of the overall device can be selected as the upstream layer. Using this approach, a portion of the membrane capacity distribution can be selected as top layer membrane, thereby reducing the range of device capacities compared to layering the membranes randomly.

Figure 8:
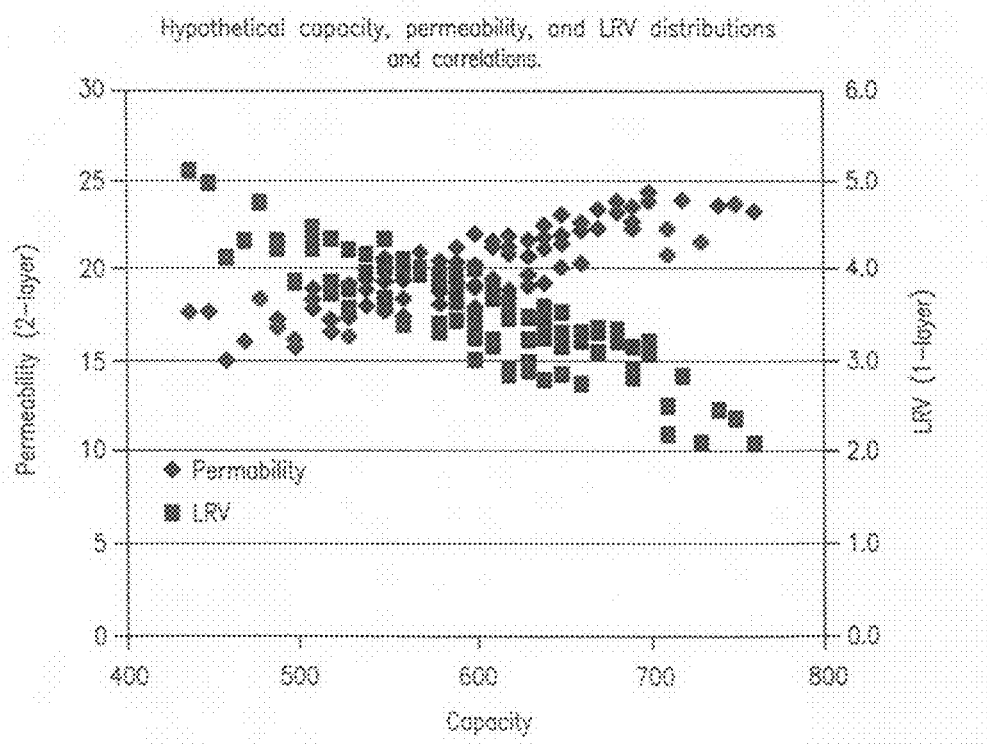
FIG. 8 is a graph of hypothetical capacity,. permeability and LRV distributions and correlations.

In view of the relative influence of the upstream membrane layer, various layering strategies are possible. Selected embodiments of the invention are described based on the FIGS. 2 and 8. FIG. 2 is a Gaussian distribution of capacity values calculated to represent membranes similar to those shown in FIGS. 5 and 6. FIG. 8 represents correlated data of permeability to capacity and LRV to capacity. To make the simulations more realistic, the points of FIG. 8 were generated from an actual linear correlation with a set degree of randomness to give the scatter plot shown. These points were then used to calculate the effects of various layering strategies.

To illustrate these strategies, a two-layer membrane device will be exemplified, although it should be understood that similar results can be obtained with devices having three or more layers. In this embodiment, a middle portion (e.g., ±10-20% of the midpoint of the distribution) of the capacity distribution is designated for the top or upstream membrane layer, with the remaining portion of the distribution to be used as the bottom layer membrane. This is illustrated graphically in FIG. 3. By utilizing a top layer membrane from the middle of the capacity distribution curve, and a bottom layer membrane from the left or right side of the capacity distribution curve, the range of device capacities will be reduced compared to random layering, with no effect on mean capacity (Table 1).

Figure 3:
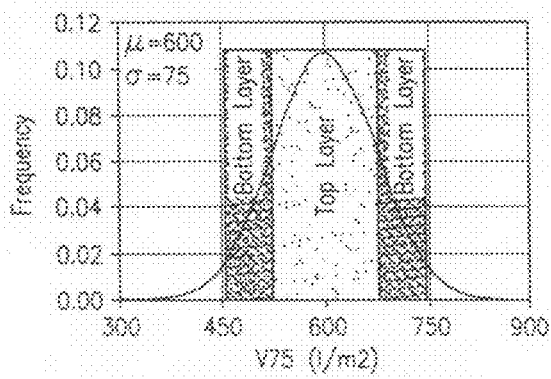
FIG. 3 is a graph of membrane capacity distribution showing a selection of top layer membrane and bottom layer membrane in accordance with certain embodiments.
Figure 4:
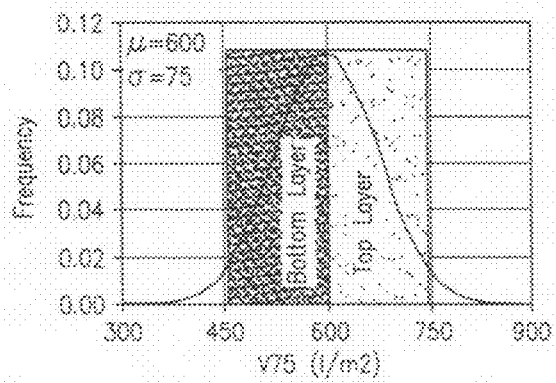
FIG. 4 is a graph of membrane capacity distribution showing another selection of top layer membrane and bottom layer membrane in accordance with certain embodiments.

FIG. 4 illustrates another embodiment of a multi-layered membrane device. In the embodiment of FIG. 4, the top layer membrane is randomly selected from the top half of the capacity distribution curve, and the bottom layer membrane is randomly selected from the bottom half of the capacity distribution curve. In addition to decreasing the capacity range by half as in the embodiment of FIG. 3, the embodiment of FIG. 4 also increases the mean capacity as compared to random layering. Because this embodiment combines the upper portion capacity distribution (and therefore the upper portion permeability distribution and the lower portion retention distribution), with lower portion capacity distribution (and therefore lower portion permeability distribution and upper portion retention distributions, respectively), and because higher capacity membranes tend to also have higher permeability and lower virus retention (but all within the product specifications) variability in permeability and retention is reduced compared to random layering (Table 1).

Those skilled in the art will appreciate that to effectively employ the embodiments of FIGS. 3 and 4, the capacity distribution must be well defined and predictable. If the actual distribution does not match the distribution assumed to establish the top and bottom layer specifications, then there will be unequal numbers of top and bottom layer membranes. The top layer capacity range could be expanded to give a safety factor in allowable top layer membrane, but this will diminish the variability reduction advantage of these strategies.

Variability in retention and permeability are also important performance factors to filter users. While capacity is controlled primarily by the top membrane layer, both layers in two-layer devices contribute to flux and retention. The resistivity (inverse of permeability) of each layer is additive.

Figure 5:
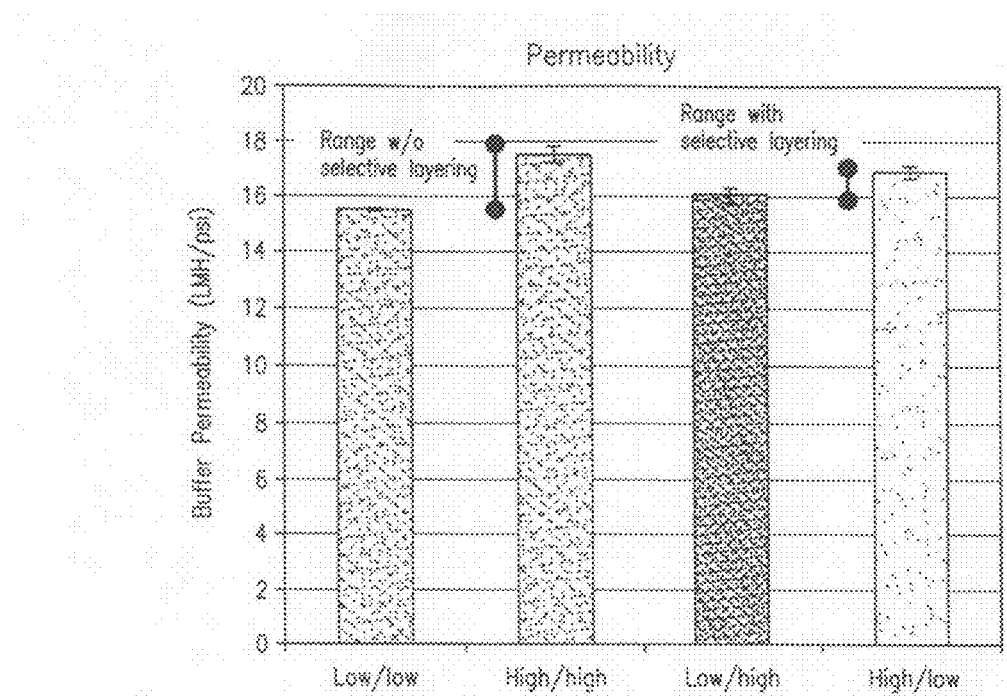
FIG. 5 is a graph showing the effect of layering on buffer permeability.
Figure 6:
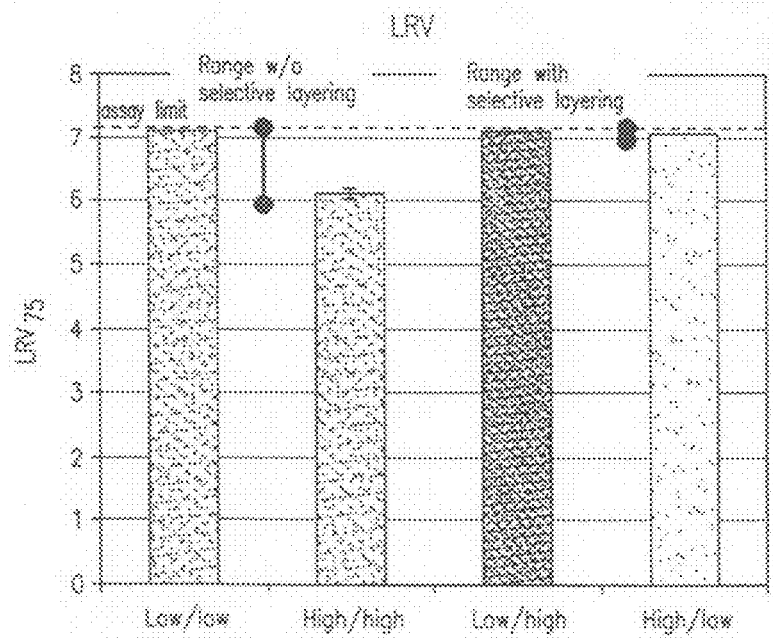
FIG. 6 is a graph showing the effect of layering on LRV.

The device retention is often expressed by the log reduction value (LRV):

$$LRV = -\log_{10}\left[\frac{C_p}{C_f}\right]$$

where C is the concentration of the target species to be retained by the membrane. LRV is generally additive for the two layers. As shown in FIGS. 5 and 6, the order of the membrane layers used in FIG. 1 does not appreciably affect two-layer permeability or the two-layer LRV.

In a preferred another embodiment, retention and permeability variability can be minimized along with capacity variability. To that end, if the capacity distribution of FIG. 2 is assumed along with the permeability and retention correlations to capacity as shown in FIG. 8 (typically, membrane capacity correlates positively with permeability and negatively with retention), the membrane layering of FIG. 7 can be employed. Thus, the top and bottom layers are paired sequentially from opposite ends of the capacity distribution curve to minimize capacity variability, permeability variability and retention variability. Specifically, the membrane with a capacity of 750 l/m² ("Top Layer 1") is combined with the membrane with a corresponding low capacity of 450 l/m² ("Bot. Layer 1") to achieve a capacity of 750 l/m², etc.

The performance variability resulting from the various embodiments was calculated for a two-layer device and compared in Table 1. It can be seen that the embodiment of FIG. 7 allows for the lowest standard deviation in permeability and retention among all of the embodiments, with only slightly higher standard deviation in capacity compared to the embodiment of FIG. 3 or random layering. The FIG. 7 embodiment also allows for higher mean capacity than the FIG. 3 embodiment. Note that the FIG. 3 embodiment can result in slightly increased permeability and retention variability compared to random layering. This occurs because the membranes with the extremes of permeability and retention are never combined with each other. The FIG. 3 embodiment does have the advantage of the lowest capacity standard deviation.

TABLE 1

| Layering Strategy | Capacity Mean | Capacity Std. Dev. | LRV Mean | LRV Std. Dev. | Permeability Mean | Permeability Std. Dev. |
|---|---|---|---|---|---|---|
| Random | 600 | 70 | 7 | 0.85 | 20 | 1.4 |
| FIG. 3 | 600 | 29 | 7 | 0.86 | 20 | 1.5 |
| FIG. 4 | 656 | 41 | 7 | 0.65 | 20 | 1.0 |
| FIG. 7 | 656 | 41 | 7 | 0.40 | 20 | 0.8 |

Figure 7:
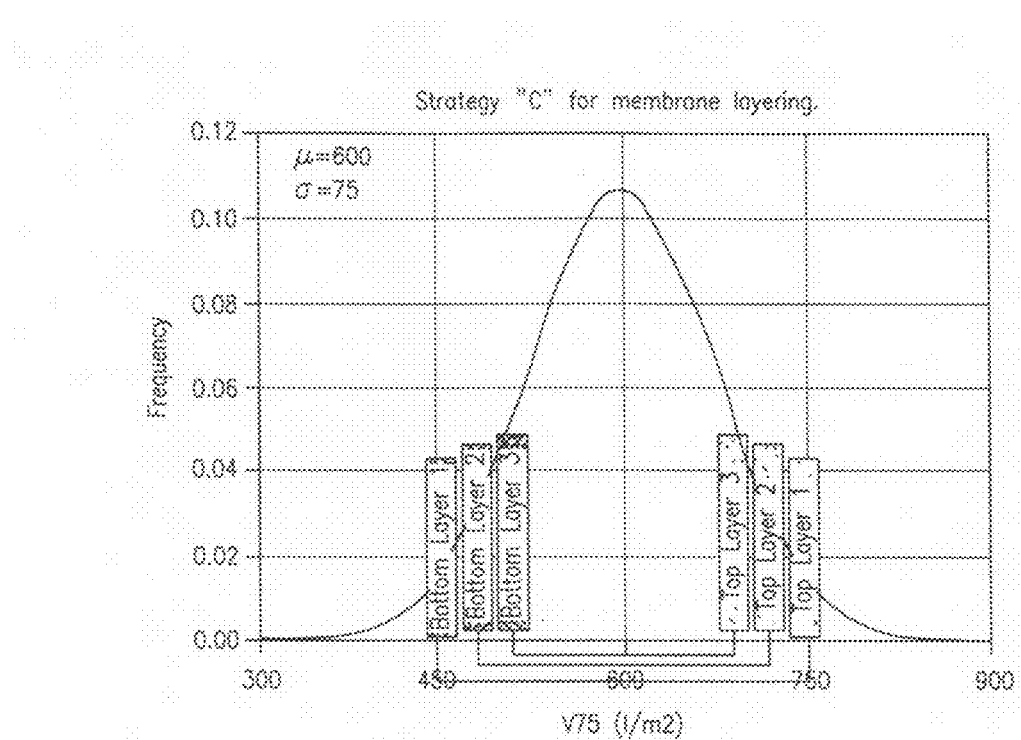
FIG. 7 is a graph of membrane capacity distribution showing a selection of top layer membrane and bottom layer membrane in accordance with certain embodiments.

In addition to the above advantages, the embodiment of FIG. 7 does not require a priori knowledge of the performance distributions as do the embodiments of FIGS. 3 and 4. Membranes can simply be paired according to this ranking system as they are available.

This method can be applied in various ways, depending on the desired output. For example, if only membranes at the very high end of capacity are available, the lower capacity membrane of these can be designated for the top layer, to give a device capacity close to the target mean, i.e., smaller range of values. If on the other hand, the maximum capacity is desired, the highest capacity membrane would be used for the top layer.

In certain preferred embodiments of carrying out the present invention, each batch of membranes produced is characterized by performance, such as by capacity. The batches are the sorted accordingly, such as in descending order of capacity value. The batches are then matched based upon capacity, such as by pairing batches by first matching those with the highest capacity to those with the lowest capacity, then by matching those with the highest capacity of the available membranes remaining with those with the lowest capacity of the available membranes, remaining, etc. (i.e., the embodiment of FIG. 7). The higher capacity layer is then designed as the upstream layer to create devices with reduced capacity variability compared to random layering.

For devices with more than two layers, alternative methods are possible. The membranes could be placed into a groups of highest, lowest and a mid-range capacity. The top layer is chosen from the highest capacity group, the bottom layer from the lowest capacity group, and the intermediate layers from the mid-range group. The intermediate layers may be chosen randomly, or the may be arranged in descending order of capacity rating, and paired off as described to fill in the layers required for the device. Alternatively the mid-range group may be sub-divided into sub-groups of descending average rating for each sub-group. The intermediate layers from second layer to second from bottom layer are then chosen from the descending capacity rating groups in order.

A calculation relating to selective layering combinations was conducted for a three-layer device using the same population of membranes used for Table 1. Because there are three layers, the capacity distribution was divided into three capacity sections (lower, center, and upper), with each section containing an equal portion of the total population.

In what is designated as embodiment A, the top (upstream) layer is selected from the middle portion of the distribution, and the middle layer and bottom (downstream) layers are selected randomly from the rest of the distribution. In what is designated as embodiment B, the top layer is selected from the middle portion of the distribution, the middle layer is selected from the upper section of the distribution, and the bottom layer is selected from the lower end of the distribution. In what is designated as embodiment C, the top layer is selected from the upper portion of the distribution, the middle layer is selected from the upper section of the distribution, and the bottom layer is selected from the lower end of the distribution. In what is designated as embodiment D, the top and bottom layers are selected as per FIG. 7, and the middle layer is selected from the center portion of the distribution.

Table 2 shows the performance variability resulting from the various embodiments. All of the embodiments are advantageous compared to random layering (the existing state of the art) with respect to either mean capacity, performance consistency, or both. Embodiment B offers the lowest capacity variability, along with low LRV and permeability variability, but with the same mean capacity as random layering. Embodiment D offers the lowest LRV and permeability variability, and has lower capacity variability and higher mean capacity than random layering. Either embodiment B or D may be preferred depending on the value placed on mean capacity compared to capacity consistency.

TABLE 2

| Layering Strategy | Capacity Mean | Capacity Std. Dev. | LRV Mean | LRV Std. Dev. | Permeability Mean | Permeability Std. Dev. |
|---|---|---|---|---|---|---|
| Random | 600 | 70 | 10.5 | 1.04 | 13.3 | 0.80 |
| A | 600 | 19 | 10.5 | 0.63 | 13.3 | 0.53 |
| B | 600 | 19 | 10.5 | 1.04 | 13.3 | 0.80 |
| C | 678 | 34 | 10.5 | 0.63 | 13.3 | 0.53 |
| D | 678 | 34 | 10.5 | 0.52 | 13.3 | 0.45 |

What is claimed is:

1. A method of reducing filter-to-filter performance variability in a multi-layered filtration device including an upstream filter membrane and a downstream filter membrane, wherein each said membrane has substantially the same pore size rating, comprising:
   a. selecting a target performance characteristic value selected from the group consisting of capacity, permeability and retention for said device;
   b. determining the values of the same performance characteristic as said target performance characteristic of a plurality of different membrane batches;
   c. selecting as said upstream membrane a membrane from said plurality of different membrane batches having a first performance characteristic value or range of values;
   d. selecting as said downstream membrane a membrane from said plurality of different membrane batches having a second performance characteristic value or range of values; wherein said first performance characteristic value or range of values is higher than said second performance characteristic value or range of values and is selected such that said target performance characteristic value is achieved.

2. The method of claim 1, wherein said performance characteristic is capacity.

3. The method of claim 1, wherein said performance characteristic is retention.

4. The method of claim 1, wherein said performance characteristic is permeability.

5. The method of claim 1, wherein said first performance characteristic is the highest performance characteristic of all membranes within said plurality of membrane batches.

6. The method of claim 5, wherein said second performance characteristic is the lowest performance characteristic of all membrane within said plurality of membrane batches.

7. The method of claim 1, wherein said first performance characteristic is the second highest performance characteristic of all membranes within said plurality of membrane batches.

8. The method of claim 7, wherein said second performance characteristic is the second lowest performance characteristic of all membrane within said plurality of membrane batches.

9. A method of reducing filter-to-filter performance variability in a multi-layered filtration device including an upstream filter membrane and a downstream filter membrane, wherein each said membrane has substantially the same pore size rating, comprising:
   a. selecting a target performance characteristic value selected from the group consisting of capacity, permeability and retention for said device;
   b. determining the values of the same performance characteristic as said target performance characteristic of a plurality of different membrane batches;
   c. selecting as said upstream membrane a membrane from said plurality of different membrane batches having a first performance characteristic value or range of values;
   d. selecting as said downstream membrane a membrane from said plurality of different membrane batches having a second performance characteristic value or range of values; wherein said first performance characteristic value or range of values is lower than said second performance characteristic value or range of values and is selected such that said target performance characteristic value is achieved.

10. The method of claim 9, wherein said performance characteristic is capacity.

11. The method of claim 9, wherein said performance characteristic is retention.

12. The method of claim 9, wherein said performance characteristic is permeability.

* * * * *